US 9,649,018 B2

(12) United States Patent
Morimoto et al.

(10) Patent No.: US 9,649,018 B2
(45) Date of Patent: May 16, 2017

(54) ENDOSCOPE SYSTEM AND METHOD FOR OPERATING THE SAME

(71) Applicant: FUJIFILM Corporation, Tokyo (JP)

(72) Inventors: Yoshinori Morimoto, Ashigarakami-gun (JP); Hiroshi Fujita, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 372 days.

(21) Appl. No.: 14/322,363

(22) Filed: Jul. 2, 2014

(65) Prior Publication Data

US 2015/0009310 A1   Jan. 8, 2015

(30) Foreign Application Priority Data

Jul. 3, 2013   (JP) .................................. 2013-139610

(51) Int. Cl.
*A61B 1/00*   (2006.01)
*A61B 1/05*   (2006.01)
(Continued)

(52) U.S. Cl.
CPC ............ *A61B 1/05* (2013.01); *A61B 1/00009* (2013.01); *A61B 1/0638* (2013.01);
(Continued)

(58) Field of Classification Search
CPC ..... A61B 1/05; A61B 1/00009; A61B 1/0638; A61B 1/0646; A61B 1/0684; A61B 5/489
See application file for complete search history.

(56) References Cited

U.S. PATENT DOCUMENTS

| 4,852,108 A * | 7/1989 | Utaka ................. H01S 5/06258 372/20 |
| 2004/0218236 A1* | 11/2004 | Kanesaka ............ H04N 5/3537 358/513 |

(Continued)

FOREIGN PATENT DOCUMENTS

| EP | 2 550 910 A1 | 1/2013 |
| JP | 4009626 B2 | 11/2007 |

(Continued)

OTHER PUBLICATIONS

Japanese Office Action and English translation thereof, dated Mar. 25, 2015, for Japanese Application No. 2014-233726.
Extended European Search Report, issued Dec. 9, 2014, for European Application No. 14175444.0.

*Primary Examiner* — Thai Tran
*Assistant Examiner* — Christopher T Braniff
(74) *Attorney, Agent, or Firm* — Birch, Stewart, Kolasch & Birch, LLP (57) ABSTRACT

A V-LED emits violet narrowband light. A G-LED emits green light. A filter limits wavelengths of the green light to pass green narrowband light. The V-LED and the G-LED are turned on alternately to apply the violet narrowband light and the green narrowband light alternately to an object. A complementary color image sensor has a Cy pixel and an Mg pixel, which are sensitive to both the violet narrowband light and the green narrowband light. The complementary color image sensor images the object under illumination of the violet narrowband light to output a first image signal and images the object under illumination of the green narrowband light to output a second image signal. Based on the first and second image signals, a special image, in which surface structure (surface blood vessels) and subsurface structure (subsurface blood vessels) are isolated from each other, is produced and displayed on a monitor.

12 Claims, 9 Drawing Sheets

(51) Int. Cl.
*A61B 1/06* (2006.01)
*A61B 5/00* (2006.01)
(52) U.S. Cl.
CPC .......... *A61B 1/0646* (2013.01); *A61B 1/0684* (2013.01); *A61B 5/489* (2013.01)

(56) References Cited

U.S. PATENT DOCUMENTS

| | | | |
|---|---|---|---|
| 2011/0071353 A1* | 3/2011 | Ozawa | A61B 1/0638 600/109 |
| 2012/0241620 A1 | 9/2012 | On | |
| 2012/0253122 A1* | 10/2012 | Minetoma | A61B 1/00057 600/109 |
| 2013/0030268 A1* | 1/2013 | Saito | A61B 1/00009 600/325 |
| 2013/0172675 A1 | 7/2013 | Yamazaki et al. | |

FOREIGN PATENT DOCUMENTS

| | | |
|---|---|---|
| JP | 2011-125404 A | 6/2011 |
| JP | 2011-206227 A | 10/2011 |
| JP | 2011-218135 A | 11/2011 |
| JP | 2012-71007 A | 4/2012 |
| JP | 2013-176 A | 1/2013 |
| JP | 2013-94489 A | 5/2013 |
| JP | 2013-111177 A | 6/2013 |
| WO | WO 2007/045077 A1 | 4/2007 |
| WO | WO 2013/042396 A1 | 3/2013 |

* cited by examiner

|  | Vn | Gn |
|---|---|---|
| Cy PIXEL | A | A |
| Mg PIXEL | A | B |
| Ye PIXEL | C | A |
| G PIXEL | C | A |

A: SENSITIVE
B: MAY BE SENSITIVE
C: NOT SENSITIVE

ENDOSCOPE SYSTEM AND METHOD FOR OPERATING THE SAME

CROSS-REFERENCE TO RELATED APPLICATIONS

The present application claims priority under 35 U.S.C. §119 to Japanese Patent Application No. 2013-139610, filed Jul. 3, 2013. Each of the above application(s) is hereby expressly incorporated by reference, in its entirety, into the present application.

BACKGROUND OF THE INVENTION

1. Field of the Invention

The present invention relates to an endoscope system for narrowband light observation with a simultaneous type image sensor and a method for operating an endoscope system.

2. Description Related to the Prior Art

It has been common to make diagnoses with the use of endoscope systems in recent medical care. The endoscope system comprises a light source device, an electronic endoscope, and a processor device. The endoscope system is used for normal light observation and narrowband light observation. In the normal light observation, visible light is used for observing an observation object inside a body cavity. In the narrowband light observation, narrowband illumination light is used. In the normal light observation, bloodstream, which represents the state of blood vessels extending in the observation object, is often unclear in the optical information obtained by the use of the visible light. In the narrowband light observation, visual identification of the state of the bloodstream or the like is improved and the state of the bloodstream of surface blood vessels is observed to determine the stage, the invasion depth, and the like of a lesion.

The narrowband light observation is performed in a frame sequential method or a simultaneous method. In the frame sequential method, blue narrowband light with the center wavelength of 415 nm±10 nm at which an extinction coefficient of hemoglobin is high and green narrowband light with the center wavelength of 540 nm±10 nm is alternately applied to the observation object. Every time each narrowband light is applied, a reflection image is captured with a monochrome image sensor. In the simultaneous method disclosed in Japanese Pat. No. 4009626, the blue narrowband light with the center wavelength of 415 nm±10 nm and the green narrowband light with the center wavelength of 540 nm±10 nm is applied simultaneously and the mixed-color light thereof is simultaneously detected with a color image sensor.

In the case where a complementary color image sensor having Cy pixels, Mg pixels, Ye pixels, and G pixels is used as an image sensor in the simultaneous method disclosed in the Japanese Pat. No. 4009626, the sensitivity of the complementary color image sensor is low on the short wavelength side. Hence, a ratio of a signal component corresponding to the blue narrowband light, of an image signal obtained by the image capture, is also low (see FIG. 7). For this reason, the contrast of the surface blood vessels is low.

Of the Cy pixels and the Mg pixels that are sensitive to the blue narrowband light, the Cy pixels are sensitive also to the green narrowband light. Hence, the blue narrowband light cannot be isolated. The Mg pixels are also somewhat sensitive to the green narrowband light so that the blue narrowband light cannot be isolated completely (see FIG. 8). The images in different layers (surface and subsurface layers) are combined and cannot be isolated from each other. As a result, the contrast of the surface blood vessels is low.

Figure 12:
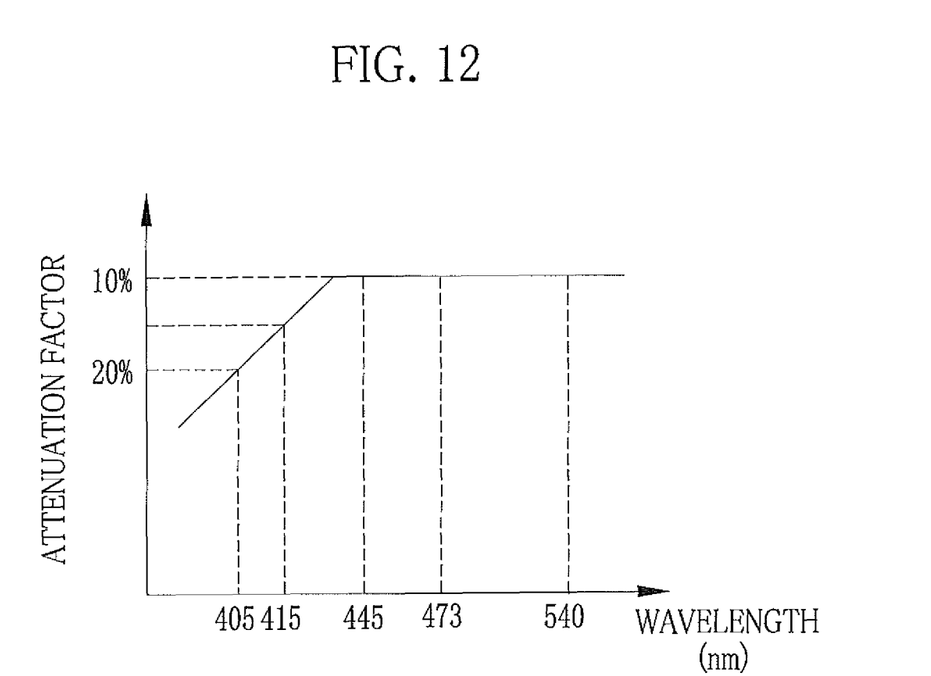
FIG. 12 is a graph illustrating spectral attenuation factor of a bundle fiber.

As for wavelength transmission properties of a bundle fiber used as a light guiding member of the endoscope, attenuation factor for light on the short wavelength side, which is less than or equal to approximately 440 nm, is high. Accordingly, the transmittance may often be reduced (see FIG. 12). In other words, in the bundle fiber, an amount of the blue narrowband light attenuated is greater than amounts of other types of narrowband light attenuated. Hence, a ratio of the signal component corresponding to the blue narrowband light to the image signal obtained by the image capture is low. As a result, the contrast of the surface blood vessels is low.

SUMMARY OF THE INVENTION

An object of the present invention is to provide an endoscope system and a method for operating an endoscope, capable of maintaining visibility of an object of interest such as surface blood vessels even in narrowband light observation with a complementary color image sensor.

In order to achieve the above and other objects, an endoscope system according to the present invention comprises an emission section, a complementary color image sensor, an image processing section, and a display section. The emission section has a first semiconductor light source for emitting first illumination light, a second semiconductor light source for emitting light of a specific wavelength range, and a narrowband filter for passing second illumination light of the light of the specific wavelength range. The first illumination light is narrowband light passing through a first transmission distance in a depth direction from a surface of an observation object. The second illumination light passes through a second transmission distance longer than the first transmission distance. The emission section applies the first illumination light and the second illumination light sequentially to the observation object. The complementary color image sensor has a specific pixel sensitive to the first and second illumination light. The complementary color image sensor images the observation object under the first illumination light and the observation object under the second illumination light, and outputs an image signal. The image processing section produces a special image based on the image signal. The display section displays the special image.

It is preferable that endoscope system further comprises a light source controller for controlling the emission section such that irradiation time of the first illumination light is longer than irradiation time of the second illumination light. It is preferable that the endoscope system further comprises an imaging controller for controlling the complementary color image sensor such that charge storage time for imaging the observation object under the first illumination light is longer than charge storage time for imaging the observation object under the second illumination light. It is preferable that the image signal includes a first image signal obtained by imaging the observation object under the first illumination light and a second image signal obtained by imaging the observation object under the second illumination light. It is preferable that the image processing section has a synchronization section for synchronizing the first image signal and the second image signal which are obtained at different timing. It is preferable that the synchronization section synchronizes a blue signal and a green signal. The blue signal is obtained by a color conversion process based on the first image signal. The green signal is obtained by a color conversion process based on the second image signal.

It is preferable that the first illumination light is violet narrowband light. The first illumination light may be blue narrowband light. It is preferable that the second illumination light is green narrowband light. The second illumination light may be green broadband light. It is preferable that the specific pixels are a cyan pixel and a magenta pixel. It is preferable that a wavelength range of the first illumination light does not overlap with a wavelength range of the second illumination light. It is preferable that the first semiconductor light source and the second semiconductor light source are turned on alternately. It is preferable that a structure at the first transmission distance and a structure at the second transmission distance are isolated from each other and visually identified in the special image.

A method for operating an endoscope system according to the present invention comprises an illumination light applying step, an imaging step, a special image producing step, and a displaying step. In the illumination light applying step, an emission section sequentially applies first illumination light and second illumination light. The emission section has a first semiconductor light source for emitting first illumination light, a second semiconductor light source for emitting light of a specific wavelength range, and a narrowband light filter for passing second illumination light of the light of the specific wavelength range. The first illumination light is narrowband light passing through a first transmission distance in a depth direction from a surface of an observation object. The second illumination light passes through a second transmission distance longer than the first transmission distance. In the imaging step, a complementary color image sensor images the observation object under the first illumination light and the observation object under the second illumination light, and outputs an image signal.

The complementary color image sensor has a specific pixel sensitive to the first and second illumination light. In the special image producing step, an image processing section produces a special image based on the image signal. In the displaying step, a display section displays the special image.

According to the present invention, the first illumination light and the second illumination light, to both of which the specific pixel of the complementary color image sensor is sensitive, is emitted sequentially, so that the first illumination light does not mix with the second illumination light in the specific pixel. Thereby the first structure at the first transmission distance of the first illumination light and the second structure at the second transmission distance of the second illumination light are isolated from each other and visually identified in the special image. Visibility of the object of the interest such as surface blood vessels is maintained without reduction.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
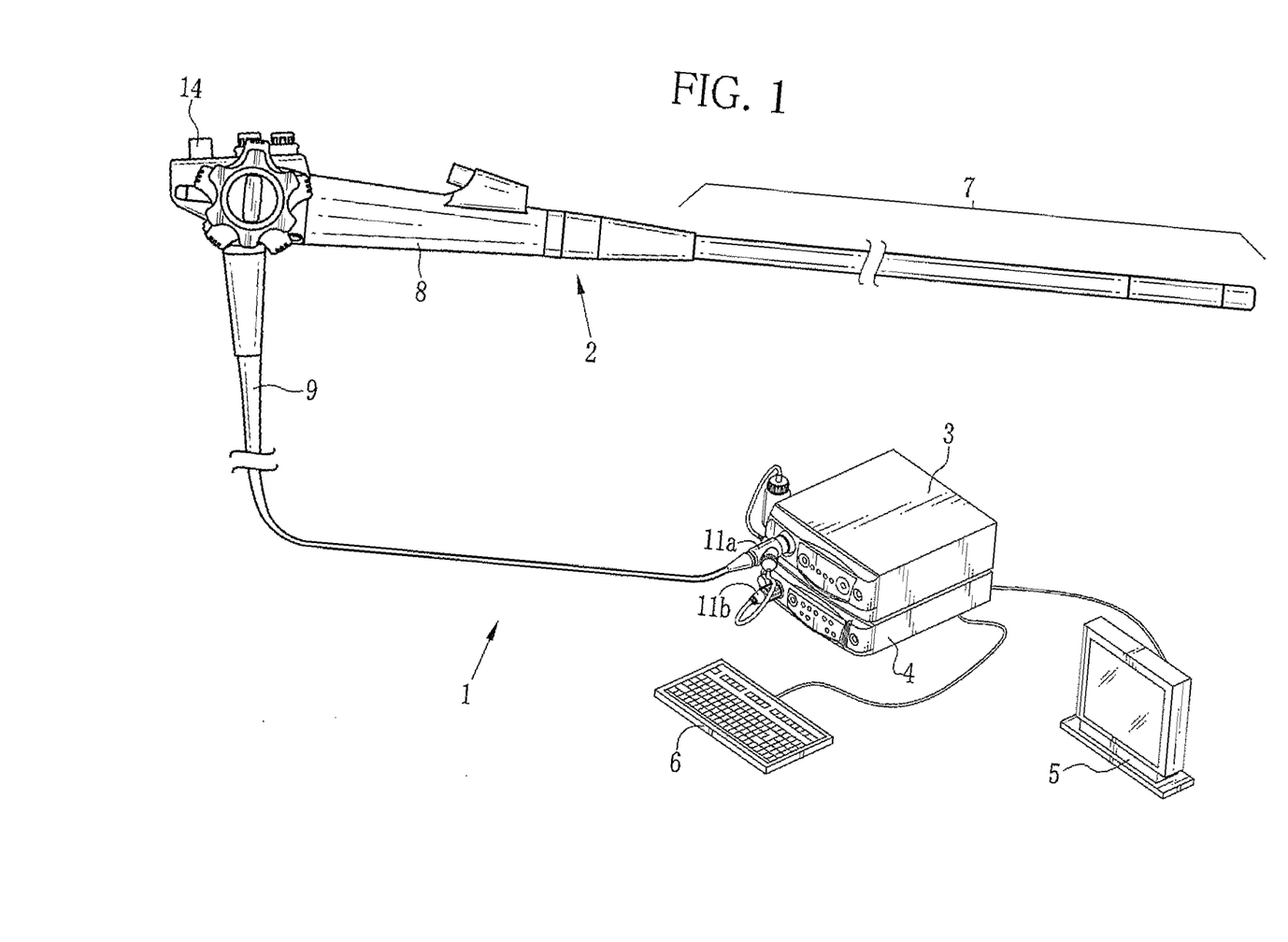
FIG. 1 is an external view of an endoscope system.

As shown in FIG. 1, an endoscope system 1 comprises an electronic endoscope (hereinafter simply referred to as the endoscope) 2, a light source device 3, a processor device 4, a monitor 5, an input device 6. The endoscope 2 is inserted into a body cavity or the like of a subject to perform endoscopy. The light source device 3 supplies illumination light to the endoscope 2. The processor device 4 drives each section of the endoscope 2. The processor device 4 processes an image signal obtained with the endoscope 2, and thereby outputs a video signal. The video signal is inputted to the monitor 5. Thus, the monitor 5 displays an image of an observation object inside the body cavity. The input device 6 inputs various types of information to the processor device 4. The endoscope 2 has a thin insertion section 7, a control handle 8 provided at the proximal end of the insertion section 7, and a universal cable 9 that extends from the control handle 8. A light guide connector 11a and a signal connector 11b are provided to an end of the universal cable 9. The light guide connector 11a is connected to the light source device 3 in a detachable manner. The signal connector 11b is connected to the processor device 4 in a detachable manner.

The endoscope system 1 has the following observation modes: a normal mode and a special mode. In the normal mode, normal light with wavelengths ranging from a blue region to a red region is used to display a normal light image on the monitor 5. In the special mode, violet narrowband light Vn and green narrowband light Gn is used to display a special image on the monitor 5. Switching from the normal mode to the special mode and vice versa is commanded by the use of a mode changeover switch 14 or the like. The mode changeover switch 14 is, for example, a scope switch or the like provided on the control handle 8 of the endoscope 2. Note that the mode changeover switch 14 may be a foot switch or provided on a front panel of the processor device 4. The mode changeover switch 14 may be composed of the input device 6.

The mode changeover switch 14 outputs a changeover signal through a mode changeover operation for changing the observation mode. The changeover signal is inputted to a control circuit 15 (see FIG. 2) in the processor device 4. Thereby, the control circuit 15 controls a light source controller 21 of the light source device 3 to allow the light source device 3 to emit the illumination light which corresponds to the chosen observation mode. The control circuit 15 controls changing the properties of a video signal processing system in the processor device 4, in association with or following the control for changing the illumination light. Thus, the properties of the video signal processing system is changed by operating the mode changeover switch 14, and thereby signal processing suitable for the normal mode or the special mode is performed.

Figure 2:
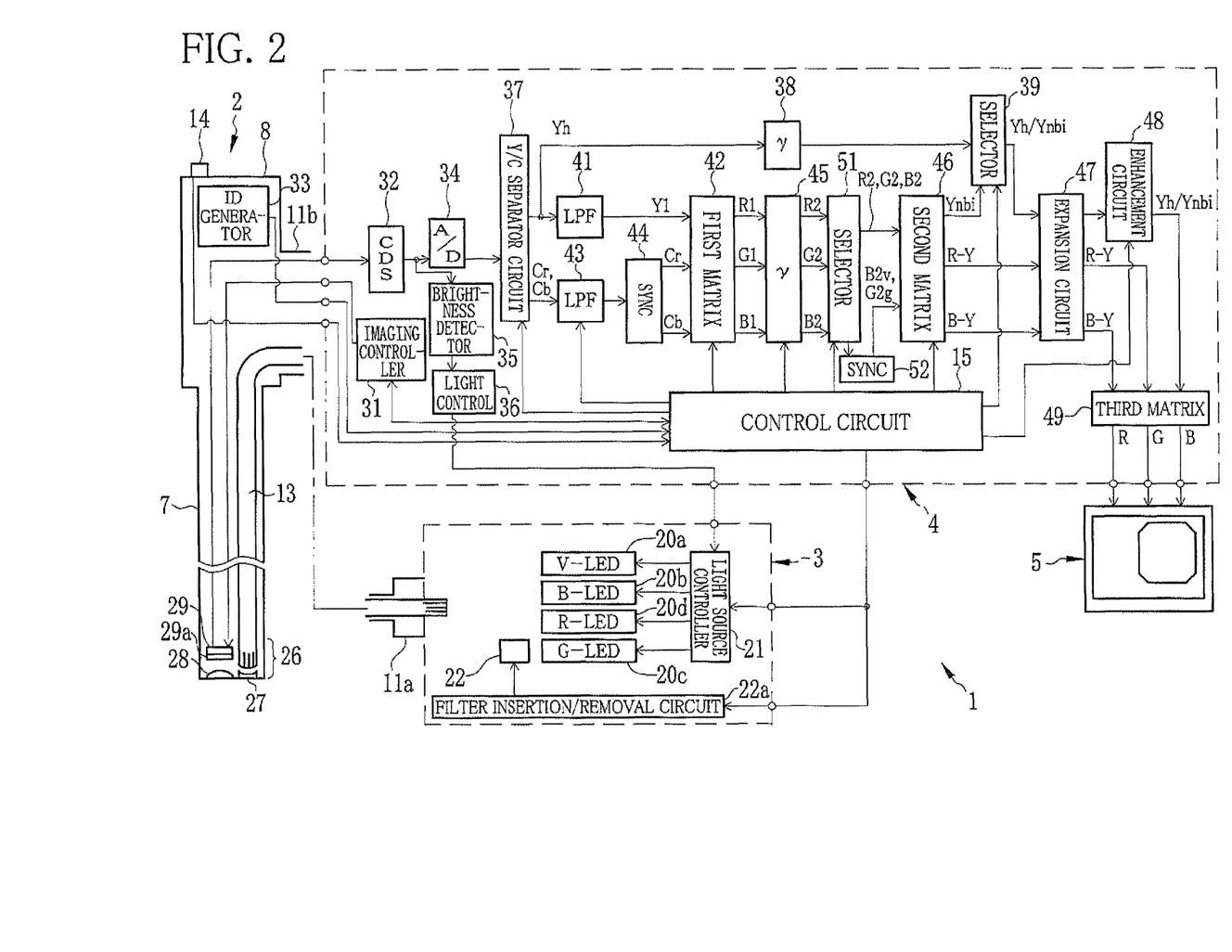
FIG. 2 is a block diagram illustrating internal configuration of the endoscope system.

As shown in FIG. 2, the light source device 3 comprises a V-LED (Violet Light Emitting Diode) 20a, a B-LED (Blue Light Emitting Diode) 20b, a G-LED (Green Light Emitting Diode) 20c, an R-LED (Red Light Emitting Diode) 20d, the light source controller 21 for driving the LEDs 20a-20d of the four colors, and a green narrowband filter 22. The green narrowband filter 22 is inserted into or retracted from a light path of the G-LED 20c. The light generated in the light source device 3 is applied to the observation object through a light guide 13 and an illumination lens 27. The light guide 13 extends inside the insertion section 7. Note that a filter insertion/retraction section 22a inserts/retracts (removes) the green narrowband filter 22 into/from the light path. The filter insertion/retraction section 22a is driven by the control circuit 15 (see FIG. 5). Note that an LD (laser diode) may be used instead of the LED. The V-LED 20a corresponds to a "first semiconductor light source" of the present invention. The G-LED 20c corresponds to a "second semiconductor light source" of the present invention. The green narrowband filter 22 corresponds to a "narrowband filter" of the present invention.

Figure 3:
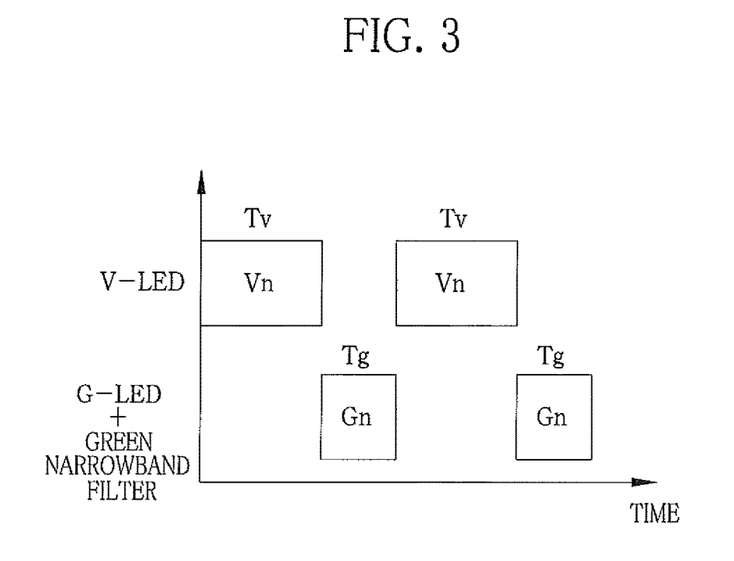
FIG. 3 is an explanatory view illustrating emission timing of violet narrowband light Vn and green narrowband light Gn and irradiation time Tv, Tg.

In the normal mode, the light source controller 21 turns on all of the V-LED 20a, the B-LED 20b, the G-LED 20c, and the R-LED 20d, in a state that the green narrowband filter 22 is retracted from the light path of the G-LED 20c, to generate the normal light. In the special mode, the V-LED 20a and the G-LED 20c are turned on alternately in a state that the green narrowband filter 22 is inserted into the light path of the G-LED 20c. Thereby the violet narrowband light Vn and the green narrowband light Gn is generated alternately. As shown in FIG. 3, the violet narrowband light Vn and the green narrowband light Gn is applied alternately to the observation object.

Here, the violet narrowband light Vn passes through a first transmission distance from the surface of the observation object to the vicinity of a surface layer of the observation object. Hence, a reflection image of the violet narrowband light Vn contains a high proportion of image components corresponding to the structures (surface blood vessels and the like) at around the first transmission distance. The green narrowband light Gn passes through a second transmission distance from the surface of the observation object to the vicinity of a subsurface layer of the observation object. Hence, a reflection image of the green narrowband light Gn contains a high proportion of image components corresponding to the structures (subsurface blood vessels and the like) at around the second transmission distance.

The light source controller 21 controls irradiation time of each of the LEDs 20a to 20d. In the normal mode, all of the LEDs 20a to 20d are kept turned on, so that the irradiation time control is unnecessary. In the special mode, irradiation time Tv of the violet narrowband light Vn is set longer than irradiation time Tg of the green narrowband light Gn. The surface blood vessels exhibit high light absorption properties with respect to the violet narrowband light Vn. In other words, in a visible region, an extinction coefficient of hemoglobin is high at the center wavelength of 405 nm±10 nm of the violet narrowband light Vn. The irradiation time Tv is extended to improve the sensitivity of a complementary color image sensor 29. As a result, the contrast of the surface blood vessels is improved. In the case where the loss of light in the blue region is significant in the light guide 13 (see FIG. 12), the irradiation time Tv of the violet narrowband light Vn is extended to compensate for the loss.

Figure 4A:
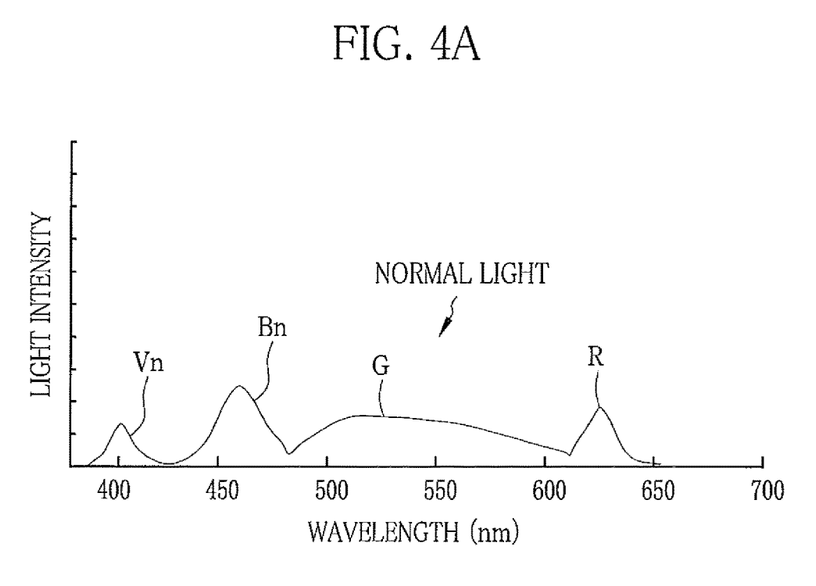
FIG. 4A is a graph illustrating emission spectrum of normal light.
Figure 4B:
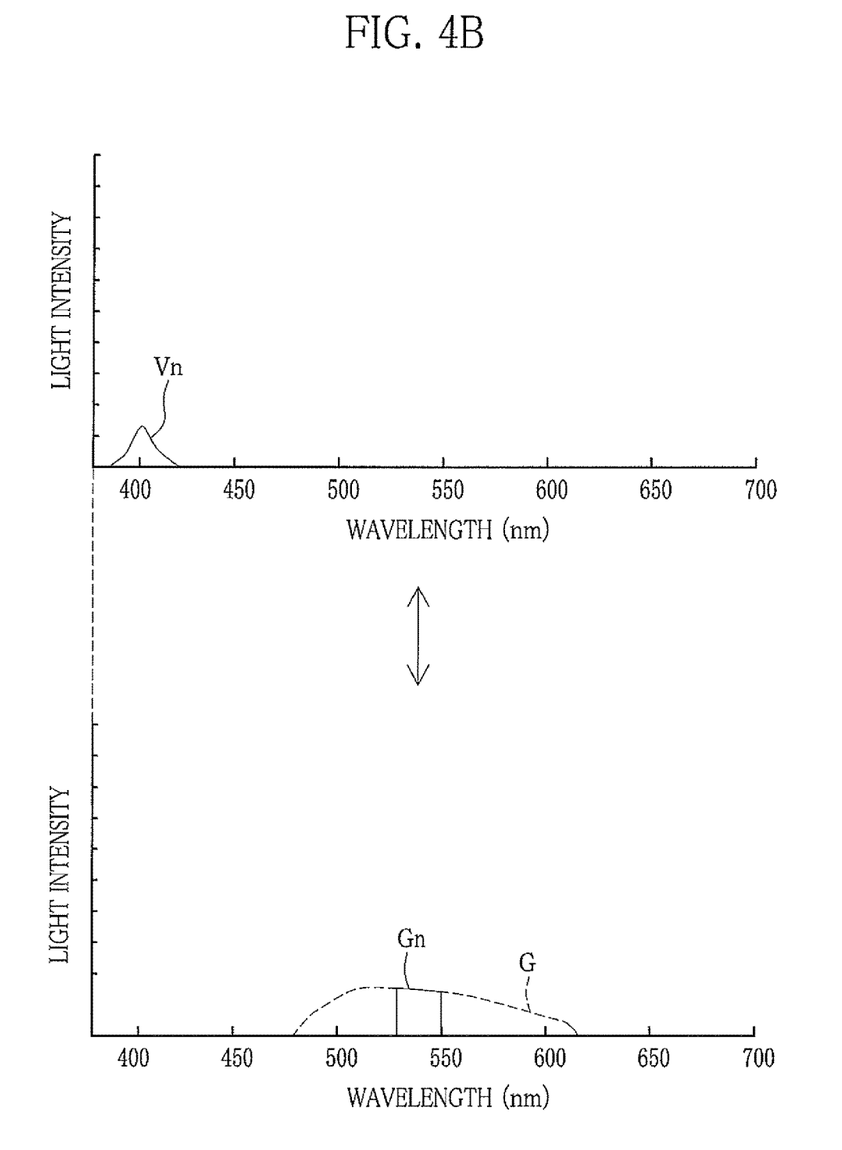
FIG. 4B is a graph illustrating emission spectra of the violet narrowband light Vn and the green narrowband light Gn.

The V-LED 20a emits the violet narrowband light Vn. The violet narrowband light Vn has a wavelength range of 380 to 440 nm, with the center wavelength of 405 nm±10 nm. The B-LED 20b emits blue-green (greenish blue) narrowband light Bn. The blue-green narrowband light Bn has a wavelength range of 420 to 500 nm, with the center wavelength of 460 nm±10 nm. The G-LED 20c emits green light G having a wavelength range of 500 to 600 nm. The R-LED 20d emits red light R having a wavelength range of 600 to 650 nm. Of the green light G emitted from the G-LED 20c, the green narrowband filter 22 passes green narrowband light of 530 to 550 nm. In the normal mode, as shown in FIG. 4A, the normal light is generated by combining the light of four colors (the violet narrowband light Vn, the blue-green narrowband light Bn, the green light G, and the red light R) with each other. In the special mode, as shown in FIG. 4B, the violet narrowband light Vn from the V-LED 20a and the green narrowband light Gn with the wavelengths limited by the green narrowband filter 22 is applied alternately to the observation object.

Note that the wavelengths of the green light G from the G-LED 20c is limited with the green narrowband filter 22, and thereby the green narrowband light Gn is generated. Instead, the wavelengths of broadband light (white light) from a semiconductor light source such as a white LED may be limited with the green narrowband filter 22 to generate the green narrowband light Gn. In other words, in the present invention, a "specific wavelength range", which is a wavelength range of the light emitted from the second semiconductor light source, may include the wavelength range (500 to 600 nm) of the green light G or the wavelength range of the broadband light such as the white light.

Figure 5:
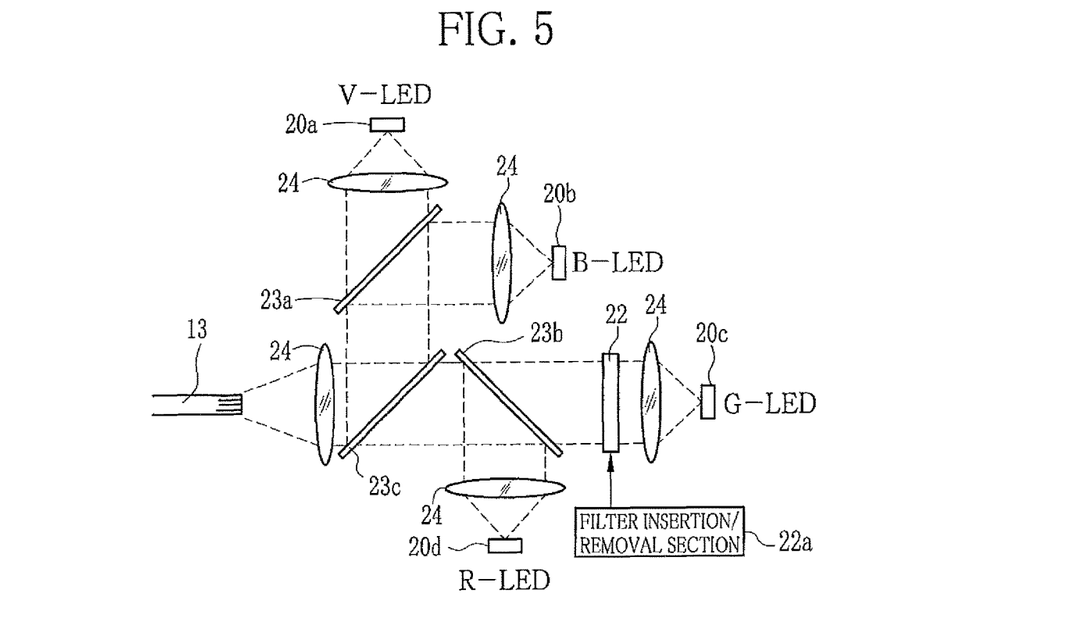
FIG. 5 is a plan view illustrating a positional relationship among a V-LED, a B-LED, a G-LED, and an R-LED and first to third dichroic mirrors.

As shown in FIG. 5, the light from the V-LED 20a, the light from the B-LED 20b, the light from the G-LED 20c, and the light from the R-LED 20d is combined with each other by the use of first to third dichroic mirrors 23a to 23c. The first dichroic mirror 23a passes the violet narrowband light Vn from the V-LED 20a while reflecting or bending the blue-green narrowband light Bn from the B-LED 20b at an angle of approximately 90°. Thus, the first dichroic mirror 23a merges a light path of the violet narrowband light Vn and a light path of the blue-green narrowband light Bn. The second dichroic mirror 23b passes the green light G or the green narrowband light Gn from the G-LED 20c while reflecting the red light R from the R-LED 20d at an angle of approximately 90°. Thus, the second dichroic mirror 23b merges a light path of the green light G or a light path of the green narrowband light Gn and a light path of the red light R. Note that a condenser lens 24 is provided between V-LED 20a and the first dichroic mirror 23a. A condenser lens 24 is provided between the B-LED 20b and the first dichroic mirror 23a. A condenser lens 24 is provided between the G-LED 20c and the second dichroic mirror 23b. A condenser lens 24 is provided between the R-LED 20d and the second dichroic mirror 23b.

The third dichroic mirror 23c reflects the violet narrowband light Vn and the blue-green narrowband light Bn from the first dichroic mirror 23a at an angle of approximately 90°, while passing the green light G or the green narrowband light Gn and the red light R from the second dichroic mirror 23b. Thereby the third dichroic mirror 23c merges the light path of the violet narrowband light Vn, the light path of the blue-green narrowband light Bn, the light path of the red light R, and the light path of the green light G (or the light path of the green narrowband light Gn). The light passed through and reflected by the third dichroic mirror 23c is incident on the light guide 13 through the condenser lens 24.

As shown in FIG. 2, in a front end portion 26 of the endoscope 2, a capture window is provided adjacent to a light window. An objective lens 28 is attached to the capture window. An optical image of the light reflected from biological tissue is formed through the objective lens 28. The complementary color image sensor 29, which is disposed at the position of the image formed by the objective lens 28, photoelectrically converts the image. Note that a CCD (Charge Coupled Device) or a CMOS (Complementary Metal-Oxide Semiconductor) sensor may be used as the complementary color image sensor 29.

Figure 6:
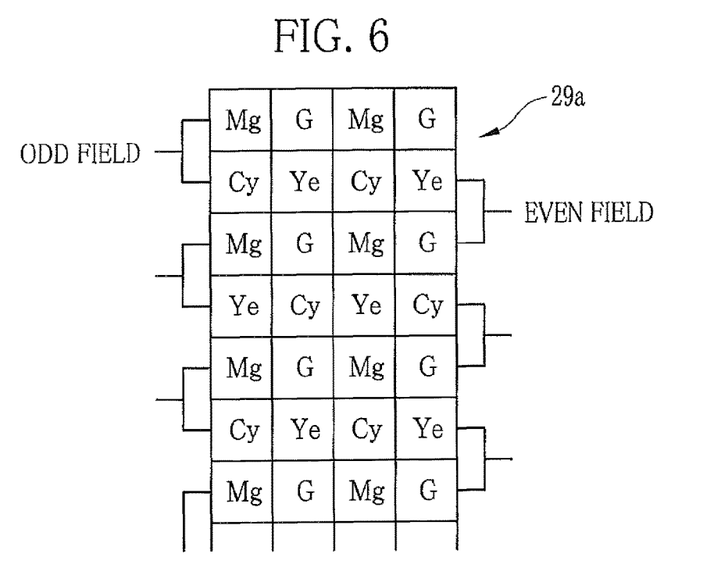
FIG. 6 is an explanatory view illustrating an array of color separation filters provided with the complementary color image sensor.

As shown in FIG. 6, a complementary color filter, being a color separation filter 29a for optical color separation, is attached on a pixel-by-pixel basis on an imaging surface of the complementary color image sensor 29. The complementary color image sensor 29 comprises pixels of four colors, magenta (Mg), green (G), cyan (Cy), and yellow (Ye). The Mg pixels and the G pixels are arranged alternately in a horizontal direction. In the vertical direction, the Mg pixel, the Cy pixel, the Mg pixel, and the Ye pixel are arranged in this order in a column. The G pixel, the Ye pixel, the G pixel, and the Cy pixel are arranged in this order in the adjacent column.

Figure 7:
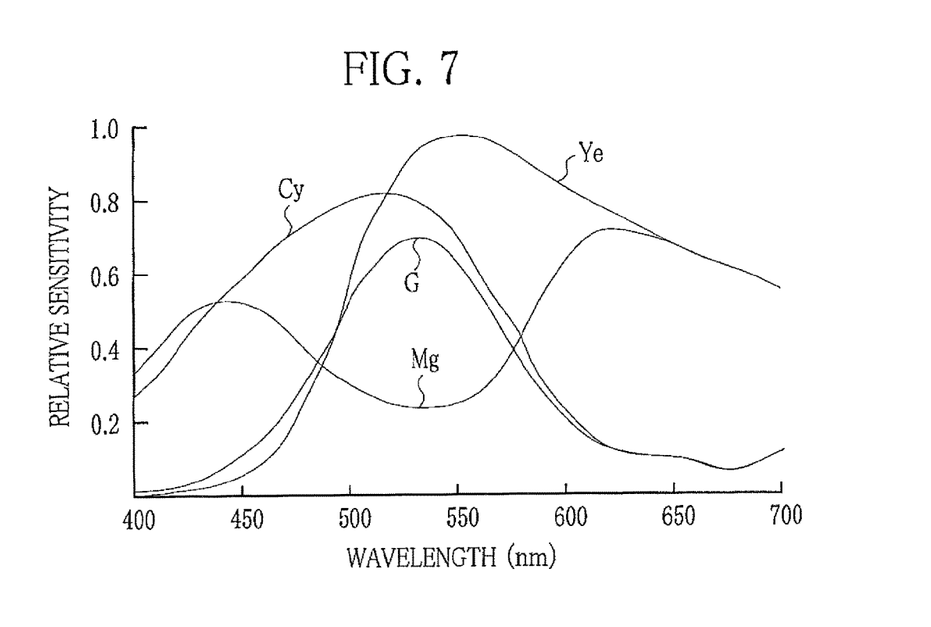
FIG. 7 is a graph illustrating relative sensitivity of each pixel in the complementary color image sensor.
Figure 8:
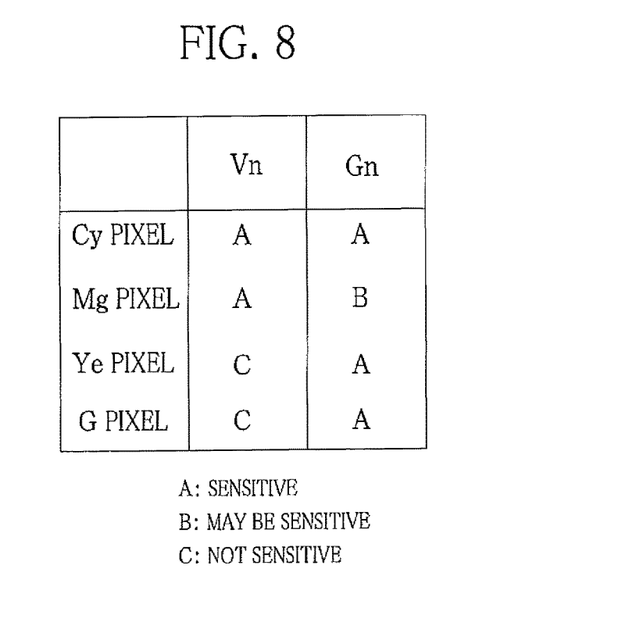
FIG. 8 is a table illustrating sensitivity, of each pixel in the complementary color image sensor, to the violet narrowband light Vn and the green narrowband light Gn.

Here, the Mg pixel, the G pixel, the Cy pixel, and the Ye pixel have their respective spectral sensitivities as shown in FIG. 7. As shown in FIG. 8, in view of the spectral characteristics, each of the Cy pixel and the Mg pixel of the complementary color image sensor 29 senses both the blue narrowband light and the green narrowband light when the blue narrowband light for enhancing blood vessels and the green narrowband light is emitted simultaneously in the conventional art disclosed in Japanese Pat. No. 4009626, for example. Hence, the narrowband light of these two colors is combined with each other and cannot be separated in each of the Cy pixel and the Mg pixel. Namely, the blue narrowband light, which contributes significantly to the improvement of the contrast of the surface blood vessels, is mixed with the green narrowband light, which contributes little to the contrast of the surface blood vessels. Hence, the contrast of the surface blood vessels, which is important for diagnosing a lesion, is reduced.

In the present invention, in the special mode, the violet narrowband light Vn, which contributes significantly to the improvement of the contrast of the surface blood vessels, and the green narrowband light Gn, which contributes little to the improvement of the contrast of the surface blood vessels but significantly to the improvement of the contrast of the subsurface blood vessels, is applied alternately (in a time-division manner). The image is captured for each irradiation (emission). Thus, the violet narrowband light Vn is not combined with the green narrowband light Gn in each of the Cy pixel and the Mg pixel. As a result, the contrast of the surface blood vessels and the contrast of the subsurface blood vessels is improved or maintained.

An imaging controller 31 drives and controls the complementary color image sensor 29. The imaging controller 31 allows reading out the signals from the complementary color image sensor 29. The signals are read out separately from an odd field and an even field (interlace reading). The signals which correspond to two rows of pixels adjacent in a vertical direction are added to each other, and then readout sequentially. The rows of the pixels which correspond to the odd field are shifted from the rows of the pixels which correspond to the even field (see FIG. 6). In the normal mode, the normal light is continuously applied to the observation object. In the special mode, the violet narrowband light Vn and the green narrowband light Gn is alternately applied to the observation object. Hence, the timing of reading a signal from the complementary color image sensor 29 is different between the normal mode and the special mode.

Figure 9:
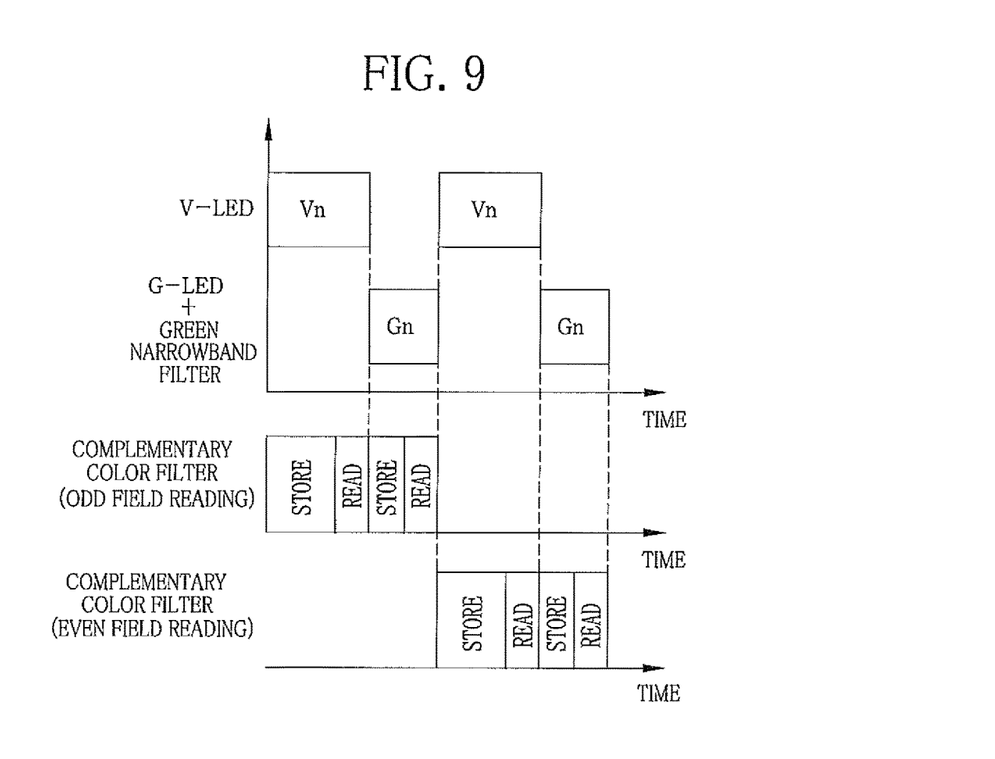
FIG. 9 is an explanatory view illustrating reading of signals from the complementary color image sensor in a special mode.

In the normal mode, the signal for the odd field and the signal for the even field are readout alternately. In the special mode, as shown in FIG. 9, reading the odd field is performed for each of the emission of the violet narrowband light Vn and the emission of the green narrowband light Gn. Namely, reading the odd field is performed twice successively. After the reading of the odd field is completed, reading the even field is performed for each of the emission of the violet narrowband light Vn and the emission of the green narrowband light Gn. Namely, reading the even field is performed twice successively. A series of readings are repeated. Note that in this embodiment, the interlace reading is performed to read out the signals from the complementary color image sensor 29. Alternatively, progressive reading may be performed. In FIG. 9, the signal is readout after each of the emission of the violet narrowband light Vn and the emission of the green narrowband light Gn. Instead, the signals may be read out after the completion of both of the emission of the violet narrowband light Vn and the emission of the green narrowband light Gn.

As shown in FIG. 2, the complementary color image sensor 29 is connected to one end of a signal line. The other end of the signal line is connected to the signal connector 11b. The signal connector 11b is connected to the processor device 4. Thus, the complementary color image sensor 29 is connected to the imaging controller 31 and a correlated double sampling circuit (hereinafter abbreviated as the CDS circuit) 32 in the processor device 4. Note that the endoscope 2 comprises an ID generator 33 for generating identification information (ID) unique to the endoscope 2. The ID from the ID generator 33 is inputted to the control circuit 15. Based on the ID, the control circuit 15 identifies the type of the endoscope 2 connected to the processor device 4, number of the pixels and the type of the complementary color image sensor 29 incorporated in the endoscope 2, and the like.

The control circuit 15 controls the imaging controller 31 to properly drive the complementary color image sensor 29 of the identified endoscope 2. The imaging controller 31 transmits information, which is related to imaging timing to drive the complementary color image sensor 29, to the control circuit 15. Based on the information related to the imaging timing, the control circuit 15 drives and controls a selector 51.

Figure 10:
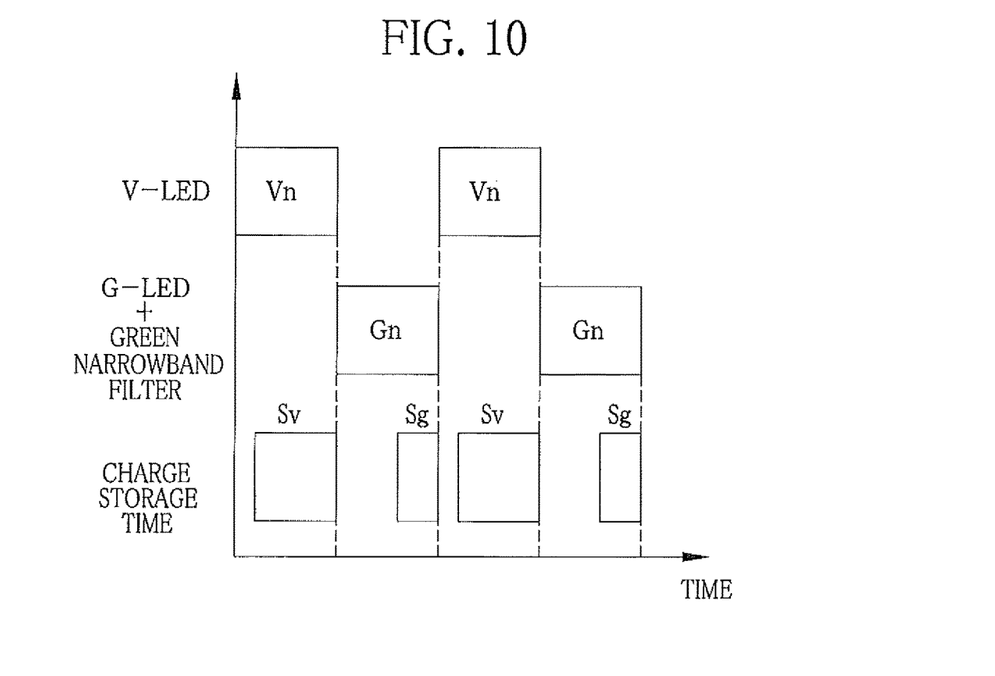
FIG. 10 is an explanatory view illustrating timing for receiving the violet narrowband light Vn and the green narrowband light Gn in the complementary color image sensor and charge storage time Sv and Sg.

The imaging controller 31 controls charge storage time of the complementary color image sensor 29. The control on the charge storage time differs according to the observation mode. In the normal mode, the given charge storage time is set. In the special mode, as shown in FIG. 10, the charge storage time Sv, which corresponds to the emission of the violet narrowband light Vn, is set longer than charge storage time Sg, which corresponds to the emission of the green narrowband light Gn.

As described above, the surface blood vessels has high light absorption properties with respect to the violet narrowband light Vn. In other words, in the visible region, the extinction coefficient of hemoglobin is high at the center wavelength of 405 nm±10 nm of the violet narrowband light Vn. Hence, the contrast of the surface blood vessels is improved by extending the charge storage time Sv to increase the sensitivity of the complementary color image sensor 29. In the case where the loss of the light in the blue region is significant in the light guide 13 (see FIG. 12), the charge storage time Sv is extended to compensate for the loss.

As shown in FIG. 2, a signal for driving the complementary color image sensor 29 is applied from the imaging controller 31 to the complementary color image sensor 29. Thereby, an imaging signal is inputted to the CDS circuit 32. The CDS circuit 32 extracts a signal component from the imaging signal and converts the signal component to a base-band signal. The base-band signal is inputted to an A/D converter circuit 34 and converted into a digital signal. The base-band signal is also inputted to a brightness detector circuit 35, which detects brightness (the average luminance of the signal).

A brightness signal, which is outputted from the brightness detector circuit 35, is inputted to a light control circuit 36. The light control circuit 36 generates a light control signal for controlling light, based on a difference between the brightness (the average luminance of the signal) and the reference brightness (a target value for light control). The light control signal from the light control circuit 36 is inputted to the light source controller 21. The light emission amounts of the V-LED 20a, the B-LED 20b, the G-LED 20c, and the R-LED 20d are controlled to achieve the reference brightness.

The digital signal outputted from the A/D converter circuit 34 is inputted to a Y/C separator circuit 37. Based on the inputted digital signal, the Y/C separator circuit 37 generates a luminance signal Y and line-sequential color difference signals, Cr(=2R−G) and Cb(=2B−G), being a color signal C in a broad sense. The luminance signal Y (which is denoted as "Yh") is inputted to a selector 39 through a γ (gamma) circuit 38 and also inputted to a first low pass filter (abbreviated as LPF) 41. The first LPF 41 limits a transmission band of the signal.

The first LPF 41 has a wide transmission band, which corresponds to the luminance signal Y. The luminance signal Y1 with the band limited according to the transmission band characteristics of the first LPF 41 is inputted to a first matrix circuit 42. The color difference signals Cr and Cb are inputted to a (line-sequential) synchronization circuit 44 through a second LPF 43, which limits the transmission band of the signals. In this case, the control circuit 15 changes the transmission band characteristics of the second LPF 43 according to the observation mode. To be more specific, in the normal mode, the transmission band of the second LPF 43 is set lower than that of the first LPF 41.

In the special mode, on the other hand, the transmission band of the second LPF 43 is set wider than the low transmission band in the normal mode. For example, the transmission band of the second LPF 43 is widened (changed) to be substantially equivalent to that of the first LPF 41. The synchronization circuit 44 generates synchronized color difference signals Cr and Cb. The color difference signals Cr and Cb are inputted to the first matrix circuit 42.

The first matrix circuit 42 performs a color conversion process on the luminance signal Y and the color difference signals Cr and Cb to output three primary color signals R, G, and B to a γ circuit 45. The first matrix circuit 42 is controlled by the control circuit 15. The control circuit 15 changes a value of a matrix coefficient, which determines the conversion characteristics, based on the color separation filter 29a of the complementary color image sensor 29 and the light emission characteristics of the V-LED 20a, the B-LED 20b, the G-LED 20c, and the R-LED 20d. Thereby the luminance signal Y1 and the color difference signals Cr and Cb are converted into the three primary color signals R1, G1, B1 with no or very little color mixing. Note that, in this embodiment, the color mixing may occur only in the normal mode. In the special mode, the color mixing does not occur because the violet narrowband light Vn and the green narrowband light Gn is emitted separately in a time-division manner.

The γ circuit 45 is also controlled by the control circuit 15. To be more specific, in the special mode, the γ characteristics are changed to enhance the characteristics of the γ correction as compared with those in the normal mode. As a result, the contrast is enhanced at the low signal levels, so that the display becomes more legible and distinguishable than that without the change in the γ characteristics. Three primary color signals R2, G2, and B2, which have been subjected to the γ correction in the γ circuit 45, are inputted to the selector 51.

The changeover of the selector 51 is controlled by the control circuit 15. In the normal mode, the selector 51 inputs the three primary color signals R2, G2, and B2 to a second matrix circuit 46. In the special mode, the selector 51 inputs a blue signal B2v, of the three primary color signals R2, G2, and B2 (hereinafter referred to as "R2v", "G2v", and "B2v") which are obtained by imaging the observation object under illumination of the violet narrowband light Vn), to a synchronization circuit 52. The remainders (the red and green signals R2v and G2v) are omitted. The selector 51 inputs a green signal G2g, of the three primary color signals R2, G2, and B2 (hereinafter referred to as "R2g", "G2g", and "B2g") which are obtained by imaging the observation object under illumination of the green narrowband light Gn, to the synchronization circuit 52. The remainders (the red and blue signals R2g and B2g) are omitted. When or after both of the blue signal B2v and the green signal G2g are inputted to the synchronization circuit 52, the synchronization circuit 52 simultaneously inputs the blue signal B2v and the green signal G2g to the second matrix circuit 46.

The second matrix circuit 46 converts the primary color signals (R2, G2, and B2, or, B2v and G2v) into a luminance signal Y and color difference signals R-Y and B-Y. In this case, in the normal mode, the control circuit 15 sets a matrix coefficient of the second matrix circuit 46 such that the three primary color signals R2, G2, and B2 are simply converted into the luminance signal Y and the color difference signals R-Y and B-Y. In the special mode, the control circuit 15 changes the matrix coefficient of the second matrix circuit 46 from that in the normal mode so as to convert the primary color signals (B2v and G2v) into a luminance signal Ynbi and color difference signals R-Y and B-Y in which the weighting of "B2v" is greater than that of "G2g".

A conversion equation of this case, using matrices A and K with 3 rows and 3 columns, is shown below.

$$\begin{pmatrix} Ynbi \\ R-Y \\ B-Y \end{pmatrix} = A * \begin{pmatrix} 0 & k1 & 0 \\ 0 & 0 & k2 \\ 0 & 0 & k3 \end{pmatrix} * \begin{pmatrix} 0 \\ G2g \\ B2v \end{pmatrix} \quad (1)$$

Here, the matrix K is composed of three real parts k1 to k3. The remaining parts are "0". The matrix A is used for converting RGB signals into color difference signals Y. A known arithmetic coefficient (2) or the like is used as the matrix A.

$$A = \begin{pmatrix} 0.299 & 0.587 & 0.114 \\ -0.299 & -0.587 & 0.886 \\ 0.701 & -0.587 & -0.114 \end{pmatrix} \quad (2)$$

The luminance signal Ynbi from the second matrix circuit 46 is inputted to the selector 39. The changeover of the selector 39 is controlled by the control circuit 15. Namely, the luminance signal Yh is selected in the normal mode. The luminance signal Ynbi is selected in the special mode.

The color difference signals R-Y and B-Y outputted from the second matrix circuit 46 and the luminance signal Yh or Ynbi (denoted as Yh/Ynbi) which passed through the selector 39 are inputted to an expansion circuit 47. The luminance signal Yh/Ynbi, which has been expanded by the expansion circuit 47, is subjected to edge enhancement by an enhancement circuit 48, and then inputted to a third matrix circuit 49. The color difference signals R-Y and B-Y, which have been expanded by the expansion circuit 47, are inputted to the third matrix circuit 49 without passing through the enhancement circuit 48. The third matrix circuit 49 converts the inputted signals into the three primary color signals R, G, and B. Then, a D/A converter circuit (not shown) converts the color signals R, G, and B into an analog video signal. The analog video signal is outputted from a video signal output end to the monitor 5. Note that the timing of reading a signal from the complementary color image sensor 29 is different between the normal mode and the special mode, so that the timing of displaying an image on the monitor 5 is also different between the normal mode and the special mode.

In the normal mode, the monitor 5 displays a normal image of an observation object illuminated with the normal light. In the special mode, the monitor 5 displays a special image of an observation object illuminated with the violet narrowband light Vn or the green narrowband light Gn. Here, the violet narrowband light Vn passes through the first transmission distance from the surface of the observation object to the vicinity of the surface layer. The green narrowband light Gn passes through the second transmission distance from the surface of the observation object to the vicinity of the subsurface layer. The second transmission distance is longer than the first transmission distance. The violet narrowband light Vn and the green narrowband light Gn is not applied simultaneously, but alternately to the observation object. Hence, the narrowband light Vn does not mix with the narrowband light Gn in the complementary color image sensor 29. The wavelength range (380 to 440 nm) of the violet narrowband light Vn does not overlap with the wavelength range (530 to 550 nm) of the green narrowband light Gn.

In the special image, the surface structure (for example, the surface blood vessels) at the first transmission distance and the subsurface structure at the second transmission distance are isolated from each other and visually identified. The contrast of the surface structure and the contrast of the subsurface structure is improved or maintained. The irradiation time Tv of the violet narrowband light Vn is longer than the irradiation time Tg of the green narrowband light Gn. The charge storage time Sv corresponding to the irradiation with the violet narrowband light Vn is longer than the charge storage time Sg corresponding to the irradiation with the green narrowband light Gn. Hence, the sensitivity of the signal obtained by the irradiation with the violet narrowband light Vn is improved. Consequently, the contrast of the surface structure, in particular, the contrast of the surface blood vessels, which are body parts important for diagnosing a lesion, is improved.

Note that the enhancement circuit 48 may change the enhancement characteristics (whether middle and low bands or middle and high bands are enhanced) or the like of the edge enhancement in accordance with the type of the complementary color image sensor 29 or the like. In particular, in the special mode, the luminance signal Ynbi is subjected to the enhancement processing. In the case where the conversion equation (1) is used, the structure of capillary vessels in the vicinity of the surface layer of the observation object is enhanced based on the signal B, which will be described below. Thus, an image component to be observed is displayed clearly.

Note that the three primary color signals R, G, and B inputted to the respective R, G, and B channels of the monitor 5 from the video signal output end are actually the signals G, B, and B in the special mode in the case where the conversion equation (1) is used. The weights assigned to the signals G, B, and B differ according to the coefficient. In particular, the ratio of the signal B is the highest, so that an endoscopic image corresponding to the structure of the surface blood vessels (capillary vessels and the like) in the vicinity of the surface layer of the observation object is displayed in a readily legible manner. Thus, the signals G, B, and B (putting aside the value of the coefficient) are actually inputted to the respective R, G, and B channels of the monitor 5 in the special mode.

In this embodiment, as described above, processing properties of a signal processing system (to be more specific, a signal processing system downstream from the Y/C separator circuit 37) of the processor device 4 change with the change in the observation mode, to perform signal processing suitable for the chosen observation mode. Hence, processing circuits exclusive for the respective observation modes are unnecessary. The use of most of the processing circuits is shared between the observation modes and only the processing properties of the processing circuits are changed to perform the processing suitable for the chosen observation mode. Thereby, the simple structure supports or is compatible with both of the observation modes.

Figure 11:
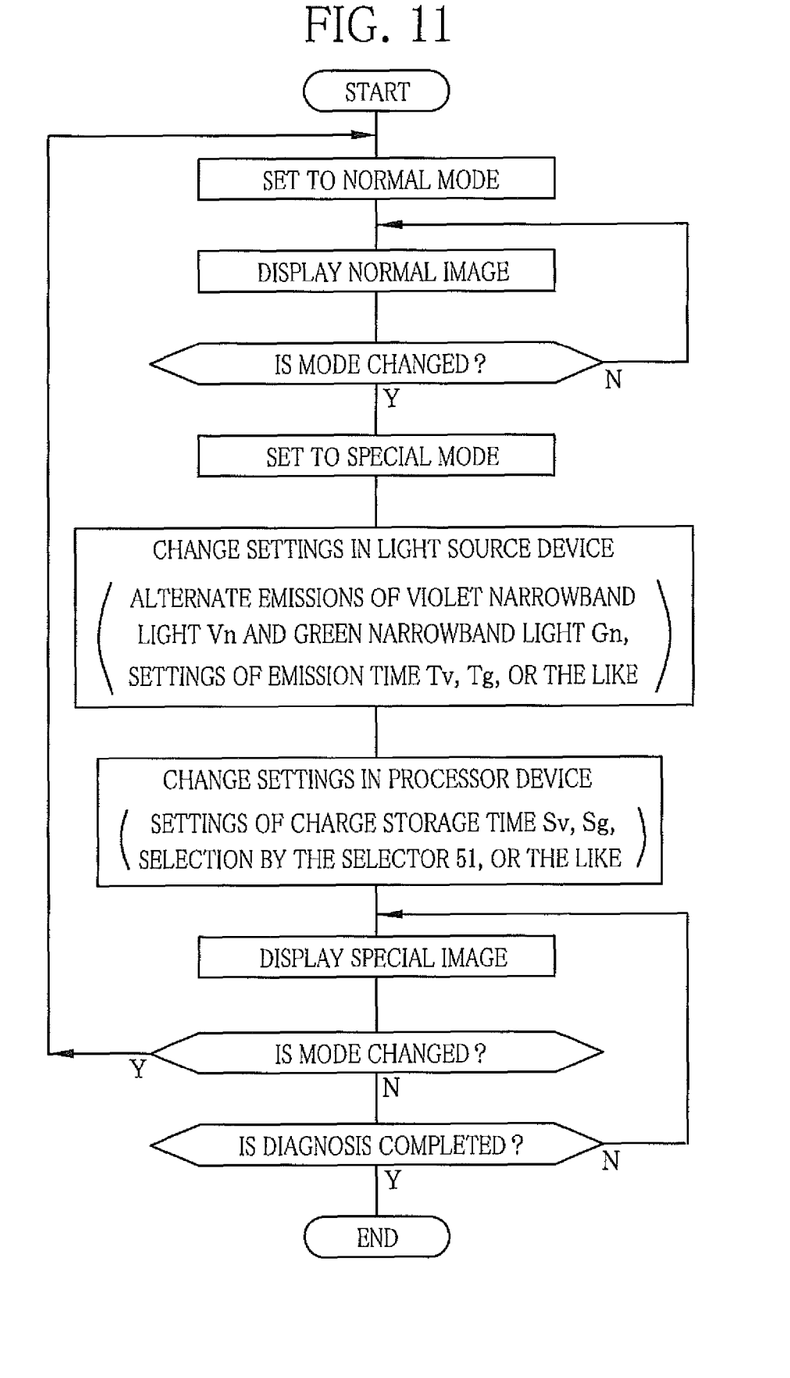
FIG. 11 is a flowchart illustrating a procedure in an embodiment.

Referring to FIG. 11, an operation of this embodiment is described below. As shown in FIG. 1, an operator connects the endoscope 2 to the light source device 3 and the processor device 4 and turns them on. The control circuit 15 of the processor device 4 starts a process for initial settings. The control circuit 15 sets each of the light source device 3 and the processor device 4 to the normal mode, for example.

In this state, the light source device 3 turns on all of the V-LED 20a, the B-LED 20b, the G-LED 20c, and the R-LED 20d. The operator inserts the insertion section 7 of the endoscope 2 into a patient's body cavity to perform endoscopic examination. The endoscope 2 captures an image under illumination of the normal light with the emission spectrum shown in FIG. 4A. Each section of the processor device 4 performs signal processing of the normal mode. The monitor 5 displays a normal image.

To observe the bloodstream and the like of the object of the interest in a lesion in the body cavity in detail, the operator operates the mode changeover switch 14. The control circuit 15 monitors whether the mode changeover switch 14 is operated. In the case where the mode changeover switch 14 is not operated, the observation mode is maintained in the normal mode. In the case where the mode changeover switch 14 is operated, the observation mode is changed to the special mode.

The control circuit 15 changes the operation mode of each of the light source device 3 and the processor device 4 to the special mode. To be more specific, the control circuit 15 controls the light source device 3 to allow the V-LED 20*a* and the G-LED 20*c* to emit the light alternately. Thereby, as shown in FIG. 4B, the violet narrowband light Vn and the green narrowband light Gn is applied alternately to the observation object. The light source controller 21 of the light source device 3 sets the irradiation time Tv of the violet narrowband light Vn longer than the irradiation time Tg of the green narrowband light Gn.

The control circuit 15 changes the settings of each section in the processor device 4. To be more specific, as shown in FIG. 10, the control circuit 15 controls the imaging controller 31 to set the charge storage time Sv for the violet narrowband light Vn longer than the charge storage time Sg for the green narrowband light Gn. The control circuit 15 widens the transmission band of the second LPF 43. The control circuit 15 changes a matrix coefficient of the first matrix circuit 42. The control circuit 15 changes the γ characteristics of the γ circuit 45.

The control circuit 15 allows the selector 51 to input the blue signal B2*v*, of the three primary color signals R2*v*, G2*v*, and B2*v* obtained by imaging the observation object under the violet narrowband light Vn, and to input the green signal G2*g*, of the three primary color signals R2*g*, G2*g*, and B2*g* obtained by imaging the observation object under the green narrowband light Gn, to the synchronization circuit 52. When or after the blue signal B2*v* and the green signal G2*g* are inputted, the synchronization circuit 52 simultaneously inputs the blue signal B2*v* and the green signal G2*g* to the second matrix circuit 46. The control circuit 15 changes the matrix coefficient of the second matrix circuit 46 so as to increase the ratio of a signal component corresponding to the blue signal B2*v*. The control circuit 15 changes the settings to allow the selector 39 to select the luminance signal Ynbi. Thereby, a special image is displayed in the special mode.

The control circuit 15 monitors whether the mode changeover switch 14 is operated. In the case where the mode changeover switch 14 is not operated, the observation mode is maintained in the special mode unless the diagnosis is ended. In the case where the mode changeover switch 14 is operated, the observation mode is returned to the normal mode.

Note that, in the special mode in the above embodiments, the green narrowband light Gn is used. Instead, the green light G with a wide wavelength range may be used without the use of the green narrowband filter 22. When the green light G is used, the narrowband light observation is performed in a bright state. In this case, note that the green narrowband filter 22 is not provided in the light source device 3.

Note that, in the special mode in the above embodiments, the violet narrowband light Vn with the center wavelength of 405 nm±10 nm is used, but the narrowband light is not limited to this. Any type of narrowband light may be used so long as the narrowband light has a high extinction coefficient of hemoglobin in a blue region. For example, blue narrowband light with the center wavelength of 445 nm±10 nm may be used instead of the violet narrowband light Vn. In this case, the wavelength range of the blue narrowband light is determined not to overlap the wavelength range (530-550 nm) of the green narrowband light G and the wavelength range (500-600 nm) of the green light G.

Note that, in the special mode in the above embodiments, the signal outputted from the γ circuit 45 is transmitted by the selector 51 to the synchronization circuit, and then the signal obtained by imaging the observation object under the violet narrowband light Vn and the signal obtained by imaging the observation object under the green narrowband light Gn are synchronized, by way of example. The synchronization may be performed in any way possible.

Note that an "emission section" in claims corresponds to a combination of the "light source device 3" and the member(s) (the light guide 13 and the like), in the endoscope 2, for guiding the light from the light source device 3 and applying the light to the observation object in this embodiment. An "image processing section" in the claims corresponds to the "processor device 4" in this embodiment. A "display section" in the claims correspond to the "monitor 5" in this embodiment.

Various changes and modifications are possible in the present invention and may be understood to be within the present invention.

What is claimed is:

1. An endoscope system comprising:
 a light source device having a first semiconductor light source for emitting first illumination light, a second semiconductor light source for emitting light of a specific wavelength range, and a narrowband filter for passing second illumination light of the light of the specific wavelength range, the first illumination light being narrowband light passing through a first transmission distance in a depth direction from a surface of an observation object, the second illumination light passing through a second transmission distance longer than the first transmission distance, the light source device applying the first illumination light and the second illumination light sequentially to the observation object;
 a complementary color image sensor having a specific pixel sensitive to the first and second illumination light, the complementary color image sensor imaging the observation object under the first illumination light and the observation object under the second illumination light, and outputting an image signal;
 a processor device for producing a special image based on the image signal; and
 a monitor for displaying the special image,
 wherein a structure at the first transmission distance and a structure at the second transmission distance are isolated from each other and visually identified in the special image.

2. The endoscope system according to claim 1, further comprising a light source controller for controlling the emission section such that irradiation time of the first illumination light is longer than irradiation time of the second illumination light.

3. The endoscope system according to claim 1, further comprising an imaging controller for controlling the complementary color image sensor such that charge storage time for imaging the observation object under the first illumination light is longer than charge storage time for imaging the observation object under the second illumination light.

4. The endoscope system according to claim 1, wherein the image signal includes a first image signal obtained by imaging the observation object under the first illumination light and a second image signal obtained by imaging the observation object under the second illumination light, and the processor device synchronizes the first image signal and the second image signal which are obtained at different timing.

5. The endoscope system according to claim 4, wherein the synchronization section synchronizes a blue signal and a green signal, and the blue signal is obtained by a color conversion process based on the first image signal, and the green signal is obtained by a color conversion process based on the second image signal.

6. The endoscope system according to claim 1, wherein the first illumination light is violet narrowband light.

7. The endoscope system according to claim 1, wherein the first illumination light is blue narrowband light.

8. The endoscope system according to claim 1, wherein the second illumination light is green narrowband light.

9. The endoscope system according to claim 1, wherein the specific pixels are a cyan pixel and a magenta pixel.

10. The endoscope system according to claim 1, wherein a wavelength range of the first illumination light does not overlap with a wavelength range of the second illumination light.

11. The endoscope system according to claim 1, wherein the first semiconductor light source and the second semiconductor light source are turned on alternately.

12. A method for operating an endoscope system comprising the steps of:

sequentially applying first illumination light and second illumination light with an emission section, the emission section having a first semiconductor light source for emitting first illumination light, a second semiconductor light source for emitting light of a specific wavelength range, and a narrowband light filter for passing second illumination light of the light of the specific wavelength range, the first illumination light being narrowband light passing through a first transmission distance in a depth direction from a surface of an observation object, the second illumination light passing through a second transmission distance longer than the first transmission distance;

imaging the observation object under the first illumination light and the observation object under the second illumination light with a complementary color image sensor having a specific pixel sensitive to the first and second illumination light, and outputting an image signal; and producing a special image based on the image signal with an image processing section; and displaying the special image with a display section, wherein a structure at the first transmission distance and a structure at the second transmission distance are isolated from each other and visually identified in the special image.

\* \* \* \* \*